(12) United States Patent
Vilarasau Alegre

(10) Patent No.: US 6,653,647 B1
(45) Date of Patent: Nov. 25, 2003

(54) SYSTEM FOR THE MICROBIOLOGICAL DISINFECTION OF AIR-CONDITIONING AND VENTILATION CONDUITS

(76) Inventor: Maria Teresa Vilarasau Alegre, Puigllancada, 28, Urb. les Pungoles, E-08459 Sant Antoni de Viamajor (ES)

( * ) Notice: Subject to any disclaimer, the term of this patent is extended or adjusted under 35 U.S.C. 154(b) by 0 days.

(21) Appl. No.: 09/582,804

(22) PCT Filed: Nov. 3, 1998

(86) PCT No.: PCT/ES98/00296

§ 371 (c)(1),
(2), (4) Date: Jun. 30, 2000

(87) PCT Pub. No.: WO00/25834

PCT Pub. Date: May 11, 2000

(51) Int. Cl.[7] .................. G01N 23/00; G01N 21/00; A61L 2/00; A62B 7/08; A47L 5/00
(52) U.S. Cl. .............. 250/504 R; 250/453.11; 250/455.11; 422/24; 422/121; 422/122; 15/304
(58) Field of Search .............. 250/504 R, 455.11, 250/453.11, 431; 422/122, 24, 121; 15/304

(56) References Cited

U.S. PATENT DOCUMENTS

| | | | | |
|---|---|---|---|---|
| 5,020,188 A | * | 6/1991 | Walton | 134/167 C |
| 5,112,370 A | * | 5/1992 | Gazzano | 422/121 |
| 5,330,722 A | * | 7/1994 | Pick et al. | 422/121 |
| 5,752,878 A | * | 5/1998 | Balkany | 422/123 |
| 5,968,455 A | * | 10/1999 | Brickley | 422/121 |

* cited by examiner

Primary Examiner—John R. Lee
Assistant Examiner—Kalimah Fernandez
(74) Attorney, Agent, or Firm—Maria Parrish Tungol; John A. Parrish

(57) ABSTRACT

This system consists of a static device (1) provided with ultraviolet ray lamps (12), fixed permanently inside the air duct (2) near the inlet in the circuit, to disinfect the incoming air flow. The system also includes a mobile device (3) to be periodically inserted inside the duct (2) and moved inside in order to fully disinfect the duct. This device consists of an axle (31), on which ultraviolet ray lamps (34) are assembled, end discs (32 and 33) provided with wheels (35 and 36) on the edge, and traction and retention cables (38 and 39).

10 Claims, 2 Drawing Sheets

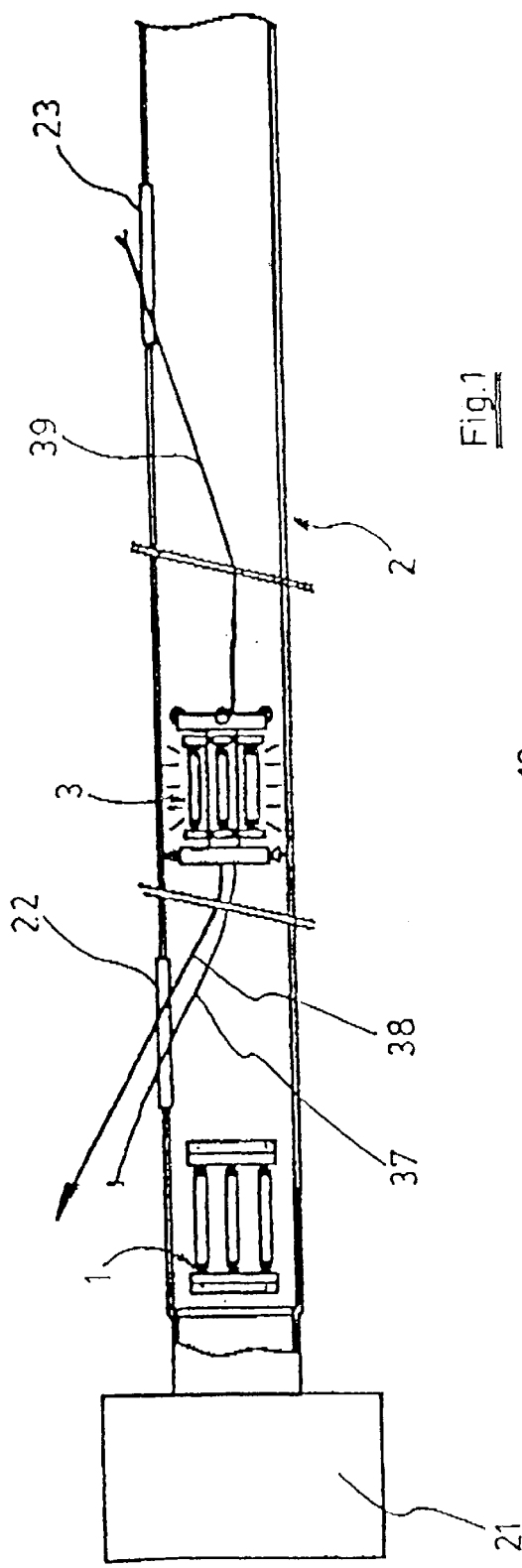
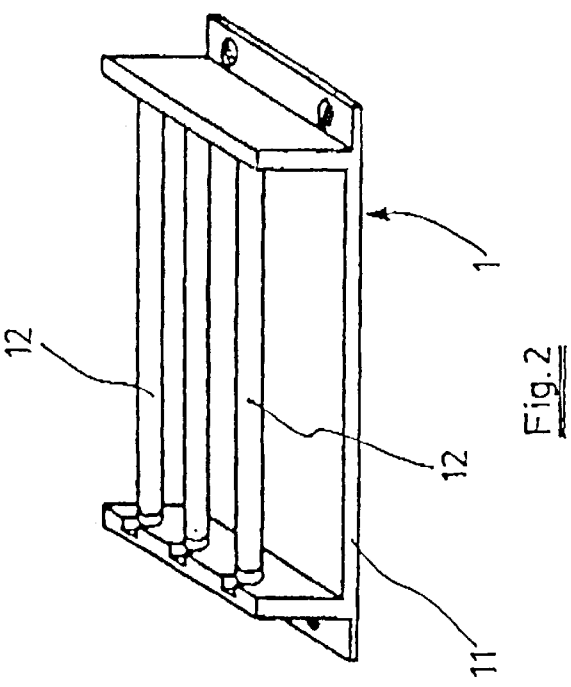

SYSTEM FOR THE MICROBIOLOGICAL DISINFECTION OF AIR-CONDITIONING AND VENTILATION CONDUITS

PURPOSE OF THE INVENTION

The system of this invention consists of a static microbiological disinfection device by ultraviolet rays, which is permanently assembled at the air inlet or inlets in the duct, so that the micro-organisms contained in the air that is projected inside the circuit by the corresponding ventilation or cooling equipment, are eliminated, plus a mobile microbiological disinfection device by ultraviolet rays, which is placed inside the duct to be cleaned, and which is moved along the length of the duct eliminating any possible micro-organisms which could be inside.

BACKGROUND TO THE INVENTION

Ventilation and air conditioning ducts are currently cleaned by combining the application of pressurised air on the inside walls with suction from outside the duct; by applying pressurised air, adhered dust particles are separated from the walls, and with suction, these particles are removed from the duct.

Although these mechanical cleaning devices provide good surface cleaning of dust particles and dirt stuck to the duct, they are not sufficient to microbiologically clean. However, it is known that micro-organisms multiply in these ducts, causing many respiratory disorders.

This microbiological cleaning method is attempted by spraying the inside of the duct with disinfectant, that can cause discomfort to certain people, or be harmful to health. Owing to its oxidising power, it can damage the ducts.

DESCRIPTION OF THE INVENTION

To solve these problems, the system that is the purpose of the invention has been designed, aimed at microbiologically cleaning the duct by emitting short-wave ultraviolet rays.

In accordance with the invention, this system is composed of at least one static device which is assembled inside the duct, near the air inlet connected to the corresponding cooling or ventilation equipment.

This static device is composed of a set of short-wave ultraviolet lamps, the purpose of which is to disinfect the air flow entering the duct. It has been planned that these lamps are connected to the corresponding cooling or ventilation equipment, and are kept on while said equipment is operating. This ensures that the incoming air does not contain micro-organisms and is not a continuous source of bacteria, fungus or other simple forms of life inside the duct.

Bearing in mind that these micro-organisms can enter the duct through the ventilation outlets, when there is no forced circulation of air inside, this system is complemented by a mobile device, inserted inside the duct from time to time, and moved inside, thereby fully disinfecting the duct.

According to the invention, this mobile device will be composed of a central axle, around which a series of short-wave ultraviolet ray lamps are assembled, and of two end discs with wheels on the edge forming the support means of the device on the inside surface of the duct.

The lamps of the mobile device are placed parallel to themselves and also to the central axle, emitting ultraviolet radiation which covers an area of 360° around the axle.

This mobile device is provided with the corresponding tubing for electric power of the lamps and two resistant cables which are fixed to the opposite ends of the device.

In order to disinfect any part of the duct, the mobile device simply has to be positioned inside, removing the electric input tubing and one of the resistant cables through one of the ventilation openings, and the remaining cable through another of the ventilation outlets.

One of these cables will be used to pull the mobile device causing it to move inside the duct, while the other cable will be used as a retainer, to prevent the device from suddenly accelerating when circulating through a slanted part or through vertical parts of the duct.

In order to fully disinfect the duct by means of the mobile device, the characteristics of the duct should first be observed, such as: type of material of which it is composed, the reflectance index, section, surface roughness, etc.

The radiation applied in each case can be achieved by varying the forward speed of the mobile device, and maintaining the power of the lamps constant, or varying the power of the lamps and maintaining the forward speed of the device constant.

In both cases, in order to set the forward speed of the device, at least one of the cables fixed to the mobile device is adjusted.

DESCRIPTION OF THE DRAWINGS

FIG. 1 shows a plan section of an air conditioning duct, with the disinfection devices included in the system that it is the object of this invention drawn inside.

FIG. 2 shows a perspective view of the static disinfection device.

PREFERENTIAL MANUFACTURE OF THE INVENTION

Figure 3:
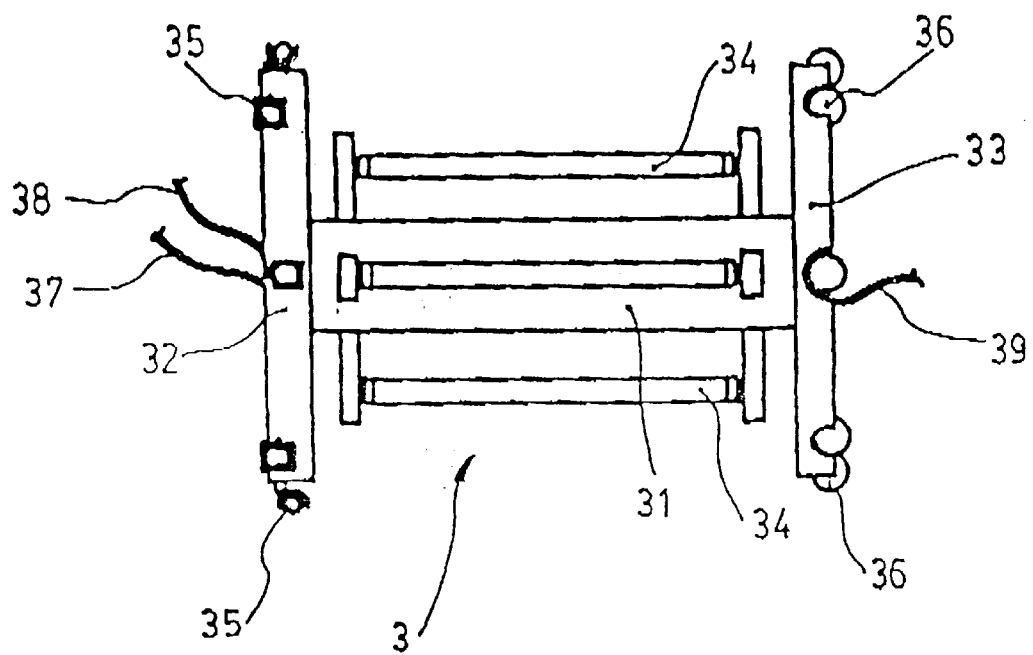
FIG. 3 shows a plan detail of the mobile disinfection device.
Figure 4:
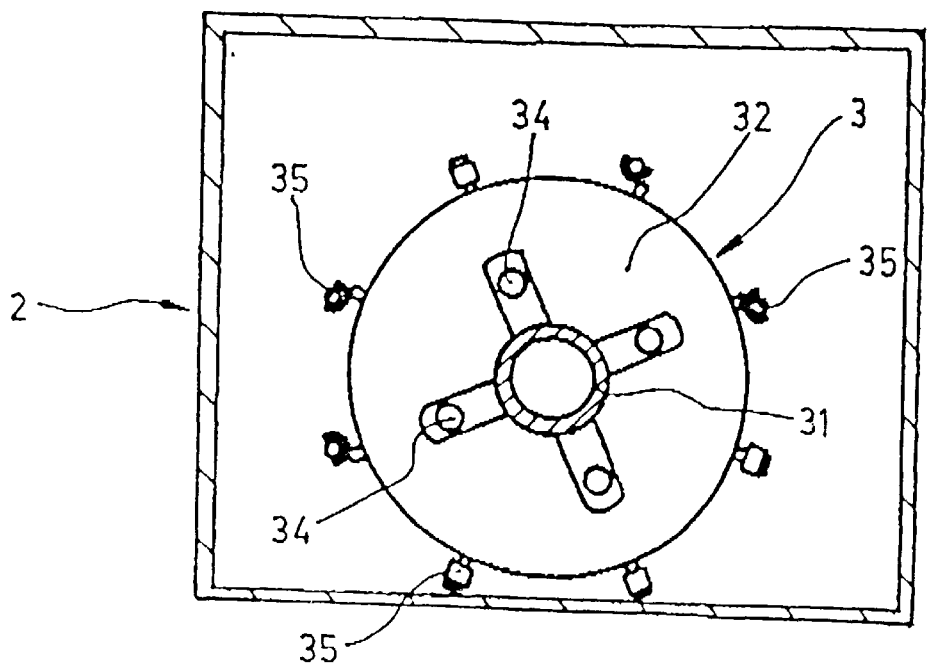
FIG. 4 shows a cross section of the same mobile device.

As can be observed in the drawings, the microbiological disinfection system that is the object of the invention, consists of a static device (1) to be fixed inside the duct (2) to disinfect the incoming air flow from cooling equipment (21) and a mobile device (3) which will be periodically used, after mechanically cleaning the ducts, to fully disinfect the duct (2).

The static device (1) consists of a support (11) provided with a series of lamp holders to assemble a set of lamps (12) which emit short-wave ultraviolet rays. This device (1) is permanently fixed inside the duct (2) near the air inlet coming from the equipment (21), and electrically connected to the equipment (21) itself, so that the lamps (12) are on when said equipment (21) is also on. In this way, the incoming air flow crosses the radiation area, removing the micro-organisms contained inside.

Bearing in mind that micro-organisms can get inside the duct (2) through the ventilation outlets (22 and 23) when the equipment (21) is off, it is necessary to periodically disinfect the whole duct (2).

This operation will be carried out by means of the mobile device (3), preferably having cleaned the inside of the duct by any known method.

The mobile device consists of an axle (31) with end discs (32 and 33). The axle (31) has lamp holders on which ultraviolet ray lamps (34) are assembled and positioned around the axle (31) and parallel to it.

The end disc (32) positioned in the front part of the device in the forward direction, has wheels (35) around its edge which are parallel to the axle (31), while the end disc (33) has wheels (36) around its edge, which are also parallel to the axle (31).

This device (3) also has tubing (37) for the electric input of the lamps (34) and two resistant cables (38 and 39) fixed on the front and back ends of the axle (31).

As can be observed in the drawing (1), in order to clean the duct (2) by means of a mobile device (3), this is inserted inside the conduct (2) so that the axle (31) is directed longitudinally and the cables (38 and 39) project outside through ventilation openings (22 and 23) respectively.

By means of cable (38), the device (3) is manually or mechanically pulled causing it to advance inside the duct (2), and it is slightly retained by cable (39) to ensure that the device (3) moves in the correct position with device axles-duct in parallel, and at a fairly constant speed, even in slanted or vertical parts of the duct (2).

Owing to the lay-out of the lamps (34) around the axle (31), the movement of the device (3) ensures that all the inside surface of the duct (2) is subject to ultraviolet radiation of sufficient intensity and duration to achieve total microbiological disinfection.

In order to control the forward speed of the device (3), it is planned that at least one of the cables (38, 39) is adjusted.

What is claimed is:

1. A system to microbiologically disinfect ventilation and air-conditioning ducts, comprising at least one static device (1) that disinfects by ultraviolet radiation, which is fixed permanently inside the duct (2) near an air inlet connected to corresponding cooling equipment (21), and a mobile device (3) that disinfects by a ultraviolet radiation, which is adapted to be inserted inside duct (2) and moved inside duct (2) in order to disinfect the duct (2) wherein the mobile device (3) includes means to cause its controlled movement inside the duct (2) and an axle (31) with end discs (32 and 33), each of the end disks having an edge, wherein the axle (31) is provided with ultraviolet ray lamps (34) and the end discs (32 and 33) are provided with wheels (35,36) on each of their edges.

2. A system according to claim 1 wherein the lamps (34) are placed around the axle (31) and parallel to it, covering a radiation area of 360° in a perpendicular plane to the axle.

3. A system according to claim 1, wherein the mobile device (3) includes tubing (37) for electrical power of the lamps (34) from outside the duct (2).

4. A system according to claim 1, wherein the discs (32, 33) are placed at the front and back ends of the mobile device in relation with the forward direction of the device (3).

5. A system, according to claim 1 wherein the revolving means mounted on the edge of the front (32) and back (33) discs are wheels (35, 36) directed parallel to the axle (31).

6. A system to microbiologically disinfect ventilation and air-conditioning ducts, comprising at least one static device (1) that disinfects by ultraviolet radiation, which is fixed inside duct (2) near an air inlet connected to corresponding cooling equipment (21), and a mobile device (3) that disinfects by ultraviolet radiation, wherein said mobile device (3) is adapted to be inserted inside the duct (2) and to move along the length of the duct (2) in order to disinfect the duct, wherein the mobile device (3) includes means to cause its controlled movement inside the duct (2) and an axle (31) with end discs (32 and 33), each of the end disks having and edge, wherein the axle (31) is provided with short-wave ultraviolet ray lamps (34) and end discs (32 and 33) are provided with wheels (35,36) on each of their edges.

7. A system according to claim 6 wherein the lamps (34) are placed around the axle (31) and parallel to it, covering a radiation area of 360° in a perpendicular plane to the axle.

8. A system according to claim 6 wherein the mobile device (3) includes tubing (37) for electrical power of the lamps (34) from outside the duct (2).

9. A system according to claim 6 wherein the end discs (32, 33) are placed at the front and back ends of the mobile device in relation with the forward direction of the device (3).

10. A system, according to claim 6 wherein the revolving means mounted on the edge of the front (32) and back (33) discs are wheels (35, 36) directed parallel to the axle (31).

* * * * *